United States Patent
Follmer et al.

(10) Patent No.: US 11,172,946 B2
(45) Date of Patent: Nov. 16, 2021

(54) APPARATUS, SYSTEM, AND METHOD FOR VASCULATURE OBSTRUCTION REMOVAL

(71) Applicant: Progressive NEURO, Inc., Santa Clara, CA (US)

(72) Inventors: Brett Allen Follmer, Santa Clara, CA (US); Edward F. Ruppel, Jr., Saratoga, CA (US)

(73) Assignee: Progressive NEURO, Inc.

( * ) Notice: Subject to any disclaimer, the term of this patent is extended or adjusted under 35 U.S.C. 154(b) by 150 days.

(21) Appl. No.: 16/663,639

(22) Filed: Oct. 25, 2019

(65) Prior Publication Data
US 2020/0129197 A1    Apr. 30, 2020

Related U.S. Application Data

(60) Provisional application No. 62/751,316, filed on Oct. 26, 2018.

(51) Int. Cl.
*A61B 17/22* (2006.01)
*A61B 17/3207* (2006.01)

(52) U.S. Cl.
CPC ............ *A61B 17/22031* (2013.01); *A61B 17/320725* (2013.01); *A61B 2017/22035* (2013.01); *A61B 2017/22038* (2013.01)

(58) Field of Classification Search
CPC .......... A61B 17/221; A61B 2017/2215; A61B 17/22031; A61B 2017/22035; A61B 2017/22038; A61B 17/320725
See application file for complete search history.

(56) References Cited

U.S. PATENT DOCUMENTS

| | | | |
|---|---|---|---|
| 4,886,061 | A | 12/1989 | Fischell et al. |
| 4,926,858 | A | 5/1990 | Gifford, III et al. |
| 5,772,674 | A | 6/1998 | Nakhjavan |
| 6,210,370 | B1 | 4/2001 | Chi-Sing et al. |
| 6,309,399 | B1 | 10/2001 | Barbut et al. |

(Continued)

FOREIGN PATENT DOCUMENTS

| | | |
|---|---|---|
| CN | 109199533 A | 1/2019 |
| DE | 19811364 A1 | 9/1999 |

(Continued)

OTHER PUBLICATIONS

International Search Report dated Jan. 9, 2020 for PCT/US2019/058153.

*Primary Examiner* — Wade Miles
(74) *Attorney, Agent, or Firm* — Nasr Patent Law LLC; Faisal K. Abou-Nasr (57) ABSTRACT

In embodiments of an obstruction removal device, system, and/or method, a removal tool and an expandable member are configured to be disposed at a distal end of a delivery tool. The removal tool may include peeler wires and hook wires that are configured to at least partially separate an obstruction from an inner surface of a vasculature. The expandable member is configured to at least partially surround the removal tool and is further configured to grasp at least one portion of the removal tool and the obstruction as the expandable member transitions from an expanded state to a contracted state when the delivery tool is removed from the vasculature to remove the removal tool and the obstruction from the vasculature.

10 Claims, 6 Drawing Sheets

(56) References Cited

U.S. PATENT DOCUMENTS

| | | |
|---|---|---|
| 6,800,085 B2 | 10/2004 | Selmon et al. |
| 7,041,117 B2 | 5/2006 | Suon et al. |
| 8,608,754 B2 | 12/2013 | Wensel et al. |
| 8,777,976 B2 | 7/2014 | Brady et al. |
| 8,801,748 B2 | 8/2014 | Martin |
| 8,986,241 B2 | 3/2015 | Evans et al. |
| 9,125,728 B2 | 9/2015 | Angel et al. |
| 9,149,609 B2 | 10/2015 | Ansel et al. |
| 9,597,171 B2 | 3/2017 | Shrivastava et al. |
| 9,833,252 B2 | 12/2017 | Sepetka et al. |
| 9,987,028 B2 | 6/2018 | Lowinger et al. |
| 10,070,878 B2 | 9/2018 | Ma |
| 10,076,347 B2 | 9/2018 | Sepetka et al. |
| 10,143,482 B2 | 12/2018 | Nguyen et al. |
| 10,172,633 B2 | 1/2019 | Martin et al. |
| 10,231,751 B2 | 3/2019 | Sos |
| 10,271,863 B2 | 4/2019 | Marks et al. |
| 10,314,600 B2 | 6/2019 | Morsi |
| 10,383,644 B2 | 8/2019 | Molaei et al. |
| 2003/0212430 A1* | 11/2003 | Bose .................... A61F 2/95 606/200 |
| 2007/0191866 A1 | 8/2007 | Palmer et al. |
| 2008/0262532 A1* | 10/2008 | Martin ............. A61B 17/32056 606/200 |
| 2009/0069828 A1* | 3/2009 | Martin ................ A61B 17/221 606/159 |
| 2009/0198269 A1 | 8/2009 | Hannes et al. |
| 2010/0131000 A1 | 5/2010 | DeMello et al. |
| 2010/0249815 A1 | 9/2010 | Jantzen et al. |
| 2011/0060359 A1 | 3/2011 | Hannes et al. |
| 2012/0197285 A1* | 8/2012 | Martin ................ A61M 25/10 606/200 |
| 2013/0006284 A1 | 1/2013 | Aggerholm et al. |
| 2014/0257245 A1 | 9/2014 | Rosenbluth et al. |
| 2015/0265299 A1 | 9/2015 | Cooper et al. |
| 2016/0361077 A1 | 12/2016 | Marks et al. |
| 2017/0290599 A1* | 10/2017 | Youn ................... A61B 17/221 |
| 2017/0325830 A1 | 11/2017 | Martin et al. |
| 2018/0008393 A1 | 1/2018 | Volobuyev et al. |
| 2018/0036028 A1 | 2/2018 | Krolik et al. |
| 2018/0140314 A1* | 5/2018 | Goyal ................. A61B 17/221 |
| 2018/0140315 A1* | 5/2018 | Bowman .......... A61B 17/22031 |
| 2018/0206865 A1 | 7/2018 | Martin et al. |
| 2018/0221037 A1 | 8/2018 | Martin et al. |
| 2018/0256177 A1 | 9/2018 | Cooper et al. |
| 2018/0271636 A1* | 9/2018 | deBeer ................. A61F 2/0105 |
| 2018/0325531 A1* | 11/2018 | Skillrud ............... A61B 17/221 |
| 2018/0325647 A1 | 11/2018 | Hauser |
| 2019/0000492 A1 | 1/2019 | Casey et al. |
| 2019/0014121 A1 | 1/2019 | Martin |
| 2019/0125396 A1 | 5/2019 | Avneri et al. |
| 2019/0239905 A1 | 8/2019 | Olson et al. |
| 2019/0298396 A1 | 10/2019 | Gamba et al. |
| 2019/0314606 A1 | 10/2019 | di Palma et al. |
| 2020/0155180 A1* | 5/2020 | Follmer .............. A61M 39/1011 |
| 2020/0214728 A1* | 7/2020 | Follmer .............. A61B 17/221 |

FOREIGN PATENT DOCUMENTS

| | | |
|---|---|---|
| EP | 1237489 A1 | 9/2002 |
| EP | 2470088 B1 | 6/2017 |
| EP | 3505091 A1 | 7/2019 |
| JP | 2018134534 A | 8/2018 |
| WO | 2014002087 A1 | 1/2014 |
| WO | 2018043279 A1 | 3/2018 |
| WO | 2018043281 A1 | 3/2018 |
| WO | 2018118706 A1 | 6/2018 |
| WO | 2018160935 A1 | 9/2018 |
| WO | 2019051425 A1 | 3/2019 |

\* cited by examiner

APPARATUS, SYSTEM, AND METHOD FOR VASCULATURE OBSTRUCTION REMOVAL

CROSS-REFERENCE TO RELATED APPLICATION

The present application claims the benefit under 35 U.S.C. § 119(e) of U.S. Provisional Application Ser. No. 62/751,316, filed Oct. 26, 2018, and titled "APPARATUS, SYSTEM, AND METHOD FOR VASCULATURE OBSTRUCTION REMOVAL," which is incorporated herein by reference in its entirety.

TECHNICAL FIELD

The present invention generally relates to medical devices, and, more particularly, to medical devices for removing vascular obstructions.

BACKGROUND

Obstruction removal systems/devices may operate by lodging the obstruction in a component of the removal system. In some cases, the obstruction may dislodge. Dislodgement of the obstruction substantially increases the risk for potential complications, such as stroke or heart attack. Thus, it is desirable to secure the obstruction safely for removal from the body.

SUMMARY

An obstruction removal system is disclosed. In one or more embodiments, the obstruction removal system includes a guide catheter configured to be inserted within a vasculature and a delivery tool having a distal end configured to be inserted within the guide catheter and disposed proximate to an obstruction in the vasculature. The obstruction removal system further includes a removal tool disposed at the distal end of the delivery tool. In one or more embodiments, the removal tool includes peeler wires and hook wires that are configured to at least partially separate the obstruction from an inner surface of the vasculature. The obstruction removal system further includes an expandable member configured to at least partially surround the removal tool. The expandable member is configured to grasp at least one portion of the removal tool and the obstruction as the expandable member transitions from an expanded state to a contracted state when the delivery tool is removed from the vasculature to remove the removal tool and the obstruction from the vasculature.

More generally, an obstruction removal device is disclosed. In one or more embodiments, the obstruction removal device includes a removal tool and an expandable member configured to be disposed at a distal end of a delivery tool. The removal tool may include peeler wires and hook wires that are configured to at least partially separate an obstruction from an inner surface of a vasculature. The expandable member is configured to at least partially surround the removal tool and is further configured to grasp at least one portion of the removal tool and the obstruction as the expandable member transitions from an expanded state to a contracted state when the delivery tool is removed from the vasculature to remove the removal tool and the obstruction from the vasculature.

A method for removing an obstruction from a vasculature is also disclosed. In one or more embodiments, the method includes the steps of: inserting a guide catheter within the vasculature; extending a delivery tool through the guide catheter so that a distal end of the delivery tool is disposed proximate to the obstruction in the vasculature; engaging at least one portion of the obstruction in the vasculature with a removal tool disposed at the distal end of the delivery tool, the removal tool comprising peeler wires and hook wires that are configured to at least partially separate the obstruction from an inner surface of the vasculature; and grasping at least one portion of the removal tool and the obstruction with an expandable member that at least partially surrounds the removal tool as the expandable member transitions from an expanded state to a contracted state when the delivery tool is removed from the vasculature to remove the removal tool and the obstruction from the vasculature.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Reference will now be made in detail to the subject matter disclosed, which is illustrated in the accompanying drawings. Referring generally to FIGS. 1A through 3C, an obstruction removal system is described, in particular, an obstruction removal system configured to selectively deploy a removal tool at least partially surrounded by an expandable member in a vasculature to reduce the risks associated with removal of an obstruction. The expandable member may be used to prevent an obstruction from dislodging from the removal tool and passing to a potentially more dangerous area (e.g. causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

Figure 1A:
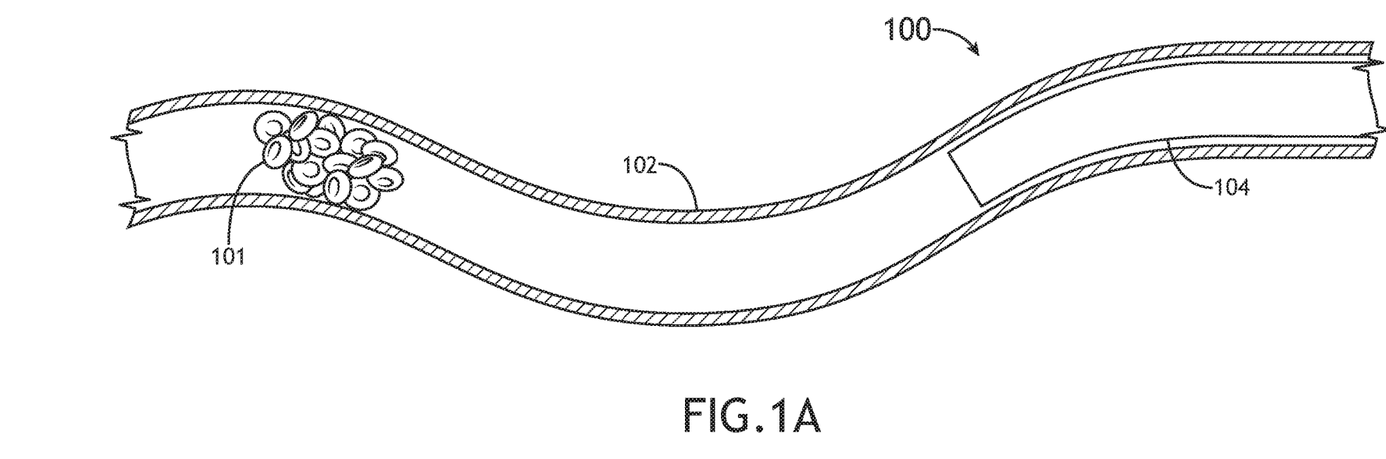
FIG. 1A illustrates a cross-sectional side view of a guide catheter of an obstruction removal system deployed within a vasculature, in accordance with one or more embodiments of the present disclosure.
Figure 1B:
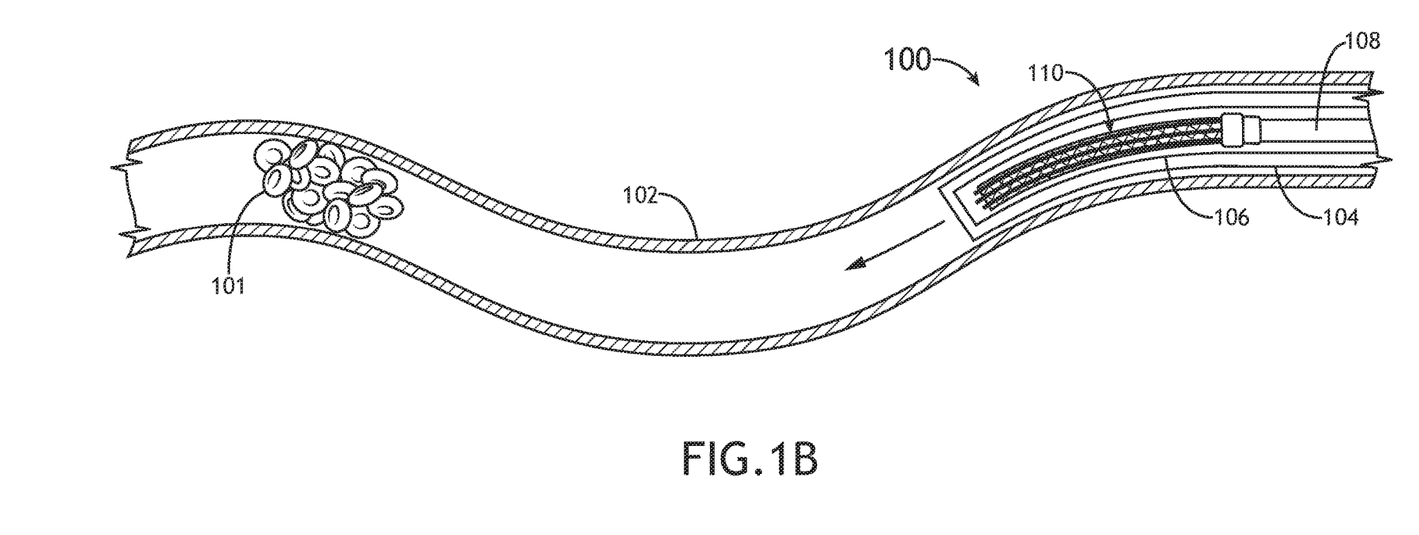
FIG. 1B illustrates a cross-sectional side view of an obstruction removal device of the obstruction removal system deployed through the guide catheter, wherein the obstruction removal device is attached to a delivery tool that is fed through the guide catheter using an intermediate catheter, in accordance with one or more embodiments of the present disclosure.

FIGS. 1A through 1F illustrate one or more embodiments of an obstruction removal system 100. As shown in FIG. 1A, the obstruction removal system 100 includes a guide catheter 104 configured to be inserted through a vasculature 102 to a position proximate to an obstruction 101. Referring now to FIG. 1B, the obstruction removal system 100 further includes an obstruction removal device 110 configured to be inserted through the guide catheter 104. For example, the obstruction removal device 110 may be coupled or formed on/near a distal end of a delivery tool 108 (e.g., a guide wire and/or tube) configured to be inserted through the guide catheter 104.

In embodiments, the obstruction removal device 110 may be at least partially housed within an intermediate catheter 106 (e.g., any suitable intermediate catheter, microcatheter, or any other suitable tube) during insertion. The intermediate catheter 106 may be used to contain and keep the obstruction removal device 110 from expanding within the guide catheter 104. This may provide one or more advantages, such as, but not limited to, reducing friction between the obstruction removal device 110 and the guide catheter 104, permitting the obstruction removal device 110 to be inserted through the distal opening of the guide catheter 104, and preventing the obstruction removal device 110 from prematurely engaging with the obstruction 101.

Figure 1C:
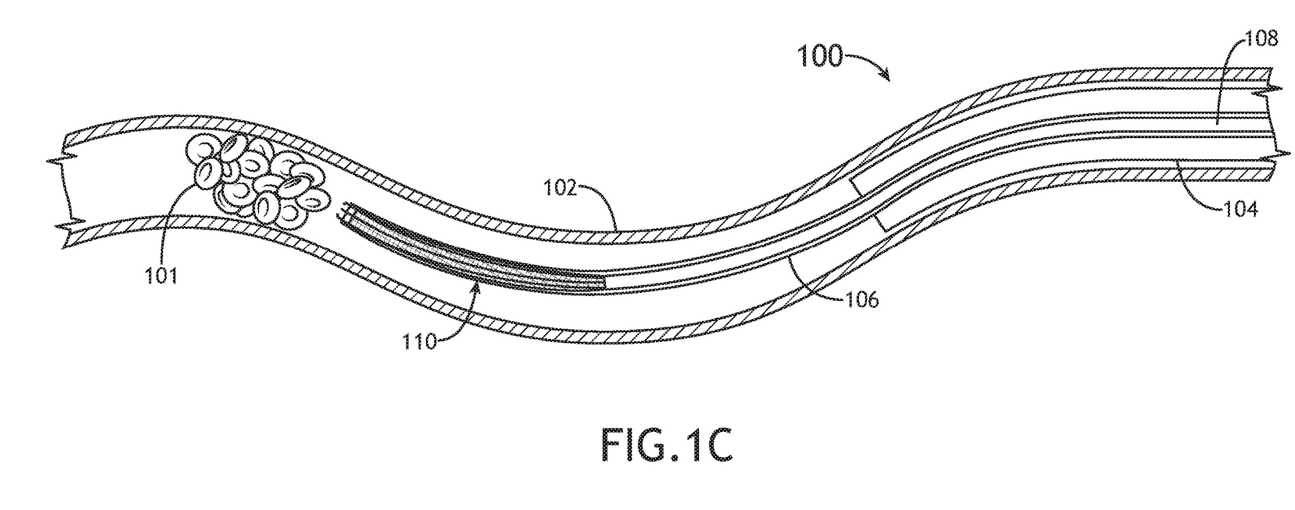
FIG. 1C illustrates a cross-sectional side view of the obstruction removal device of the obstruction removal system deployed within the vasculature in proximity to an obstruction, in accordance with one or more embodiments of the present disclosure.

FIG. 1C illustrates the obstruction removal device 110 deployed within the vasculature 102 in proximity to an obstruction 101. The delivery tool 108 (e.g., a guide wire and/or tube) is configured to be inserted within the guide catheter 104 and disposed proximate to the obstruction 101 in the vasculature 102. For example, the delivery tool 108, carrying the end-mounted obstruction removal device 110, may be fed through the guide catheter 104 using the intermediate catheter 106 to contain/sheathe the obstruction removal device 110 during its insertion.

Figure 1D:
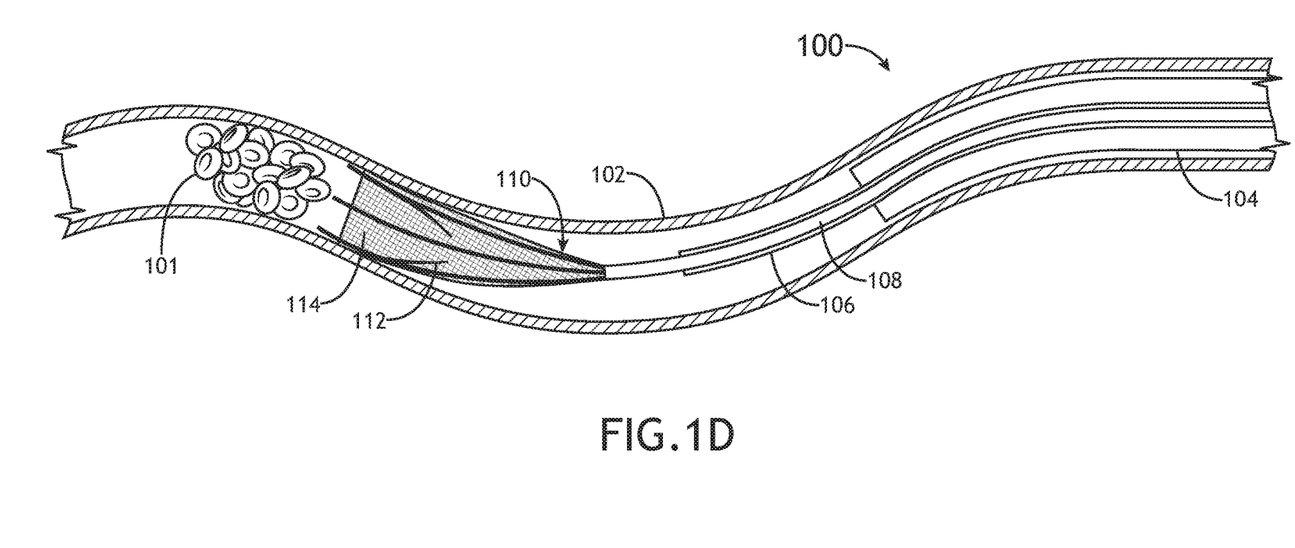
FIG. 1D illustrates a cross-sectional side view of the obstruction removal device of the obstruction removal system deployed within the vasculature, wherein the intermediate catheter is pulled back (and/or the delivery tool is pushed forward) to unsheathe the obstruction removal device so that the obstruction removal device can engage the obstruction in the vasculature, in accordance with one or more embodiments of the present disclosure.

Referring now to FIG. 1D, the intermediate catheter 106 may be configured to unsheathe the obstruction removal device 110 so that the obstruction removal device 110 can engage the obstruction 101 in the vasculature 102. For example, after reaching a desired position within the vasculature 102, the intermediate catheter 106 may be pulled back (and/or the delivery tool 108 may be pushed forward relative to the intermediate catheter 106) to unsheathe the obstruction removal device 110 so that the obstruction removal device 110 can engage the obstruction 101.

Figure 2:
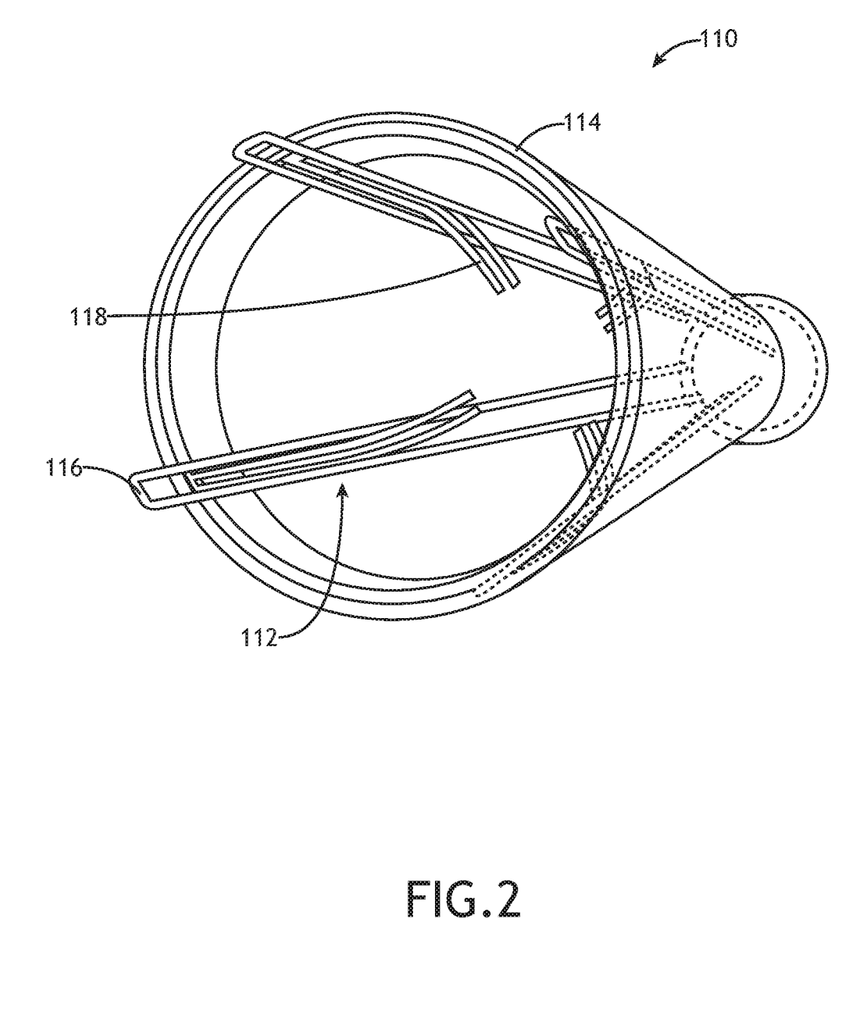
FIG. 2 illustrates a perspective view of the obstruction removal device, in accordance with one or more embodiments of the present disclosure.

As shown in FIG. 2, the obstruction removal device 110 may include a removal tool 112 comprising peeler wires 116 and hook wires 118 that are configured to at least partially separate the obstruction 101 from an inner surface of the vasculature 102. In embodiments, the peeler wires 116 comprise wire segments that extend from the distal end of the delivery tool 108 toward the inner surface of the vasculature 102 when the removal tool 112 is deployed within the vasculature 102. The hook wires 118 comprise wire segments that extend from respective wire segments of the peeler wires 116 toward a central axis of the removal tool 112. For example, the hook wires 118 may be curved toward the central axis of the removal tool 112, thereby forming hook-like or barb-like structures that are configured to catch onto and secure the obstruction 101 after the peeler wires 116 separate the obstruction 101 from the inner surface of the vasculature 102.

The obstruction removal device 110 may further include an expandable member 114 configured to at least partially surround the removal tool 112. In embodiments, the expandable member 114 is configured to grasp at least one portion of the removal tool 112 and the obstruction 101 as the expandable member transitions from an expanded state to a contracted state, e.g., when the delivery tool 108 is withdrawn through the guide catheter 104 to remove the removal tool 112 and the obstruction 101 from the vasculature 102.

As the removal tool 112 is pushed toward the obstruction, the peeler wires 116 begin separating the obstruction 101 from the inner surface of the vasculature 102. At this stage, the expandable member 114 may also assist in separating the obstruction 101 from the inner surface of the vasculature 102. In some implementations, the system may be torqued to aid in advancement of the removal tool 112 and/or expandable member 114. Meanwhile the hook wires 118 are configured to catch onto and secure the obstruction 101.

Figure 1E:
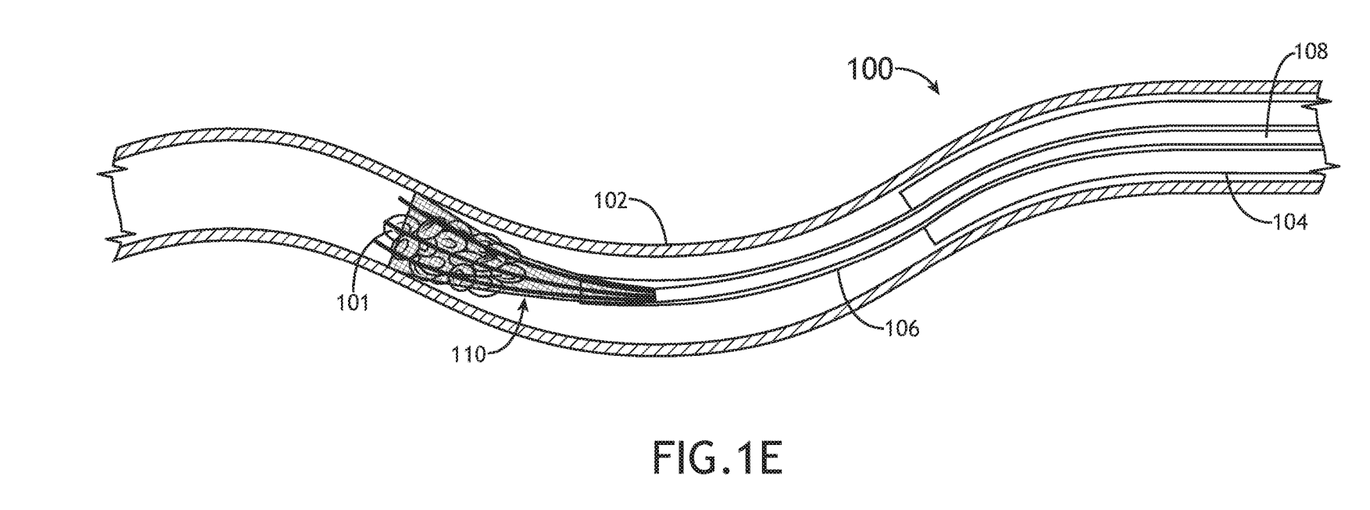
FIG. 1E illustrates a cross-sectional side view of the obstruction removal device of the obstruction removal system deployed within the vasculature, wherein the intermediate catheter is pushed forward (and/or the delivery tool is pulled back) to at least partially re-sheathe the obstruction removal device so that the obstruction removal device grasps the obstruction, in accordance with one or more embodiments of the present disclosure.

The intermediate catheter 106 may be pushed forward (and/or the delivery tool 108 may be pulled back) to at least partially re-sheathe the obstruction removal device 110 so that the removal tool 112 of the obstruction removal device 110 grasps the obstruction 101. For example, as shown in FIG. 1E, after engaging the obstruction 101 with the removal tool 112 of the obstruction removal device 110, the intermediate catheter 106 may be pushed forward (and/or the delivery tool 108 may be pulled back relative to the intermediate catheter 106) to at least partially re-sheathe the obstruction removal device 110 so that the expandable member 114 compresses the removal tool 112, thereby causing the removal tool 112 to grasp/clench the obstruction 101.

Figure 1F:
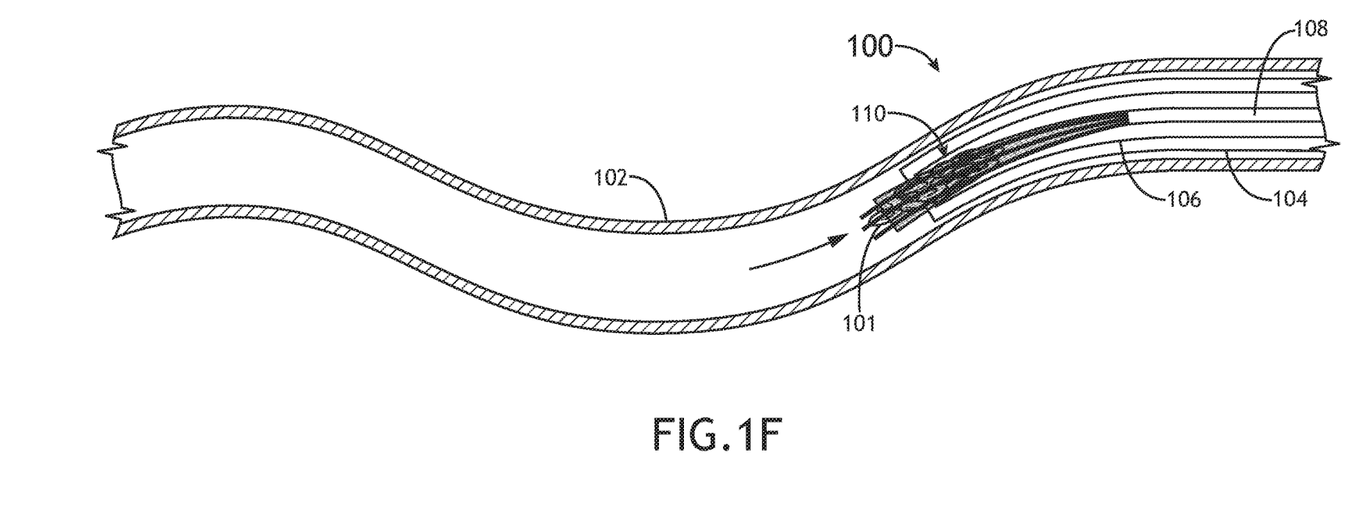
FIG. 1F illustrates a cross-sectional side view of the obstruction removal device and the intermediate catheter of the obstruction removal system being pulled back through the guide catheter to remove the obstruction from the vasculature, in accordance with one or more embodiments of the present disclosure.

As shown in FIG. 1F, the intermediate catheter 106 with the delivery tool 108 and obstruction removal device 110 are then pulled back through the guide catheter 104 to remove the obstruction 101 from the vasculature 102. The delivery tool 108 with the obstruction removal device 110 (including removal tool 112 and expandable member 114) and the obstruction 101 may be withdrawn through the intermediate catheter 106, as depicted in FIG. 1F. Alternatively, the delivery tool 108 with the obstruction removal device 110 and the obstruction 101 may be pulled directly through the guide catheter 104 (without use of an intermediate catheter 106).

As noted above, the expandable member 114 may be configured to transition between contracted/collapsed and expanded states. The expandable member 114 may be configured to transition between the contracted and expanded states in any suitable way, including, but not limited to, unsheathing the expandable member 114 to allow expansion and sheathing/re-sheathing the expandable member 114 to induce contraction.

The expanded state may allow the expandable member 114 to surround at least a portion of the removal tool 112 and/or the obstruction 101. The contracted state may be suitable for insertion and removal of the obstruction removal device 110 (including expandable member 114 and removal tool 112) through the guide catheter 104 and/or intermediate catheter 106. For example, when the expandable member 114 is in the collapsed/contracted state, after surrounding at least a portion of the removal tool 112 and/or the obstruction 101, the expandable member 114 and the removal tool 112 may be withdrawn through the guide catheter 104 and/or the intermediate catheter 106 to remove the obstruction 101 from the vasculature 102.

Benefits of surrounding at least a portion of the removal tool 112 and/or the obstruction 101 with the expandable member 114 may include, but are not limited to, smaller cross-sectional area, reduced friction on a vessel wall, reduced likelihood of catching on an opening of the guide catheter 104 and/or intermediate catheter 106, and reduced likelihood of obstruction dislodgement.

As shown in FIGS. 1A through 1F, the delivery tool 108 may be a guide wire or tube with the expandable member 114 and the removal tool 112 both fixed to the distal end of the guide wire or tube. Furthermore, the removal tool 112 may be fixedly/permanently coupled to the expandable member 114. In other embodiments, such as the embodiments illustrated in FIGS. 3A through 3C, the removal tool 112 and the expandable member 114 are separable and/or moveable independent of one another. For example, the delivery tool 108 may include a guide wire 108A disposed within a tube 108B, where the removal tool 112 is fixed to the distal end of the guide wire 108A, and the expandable member 114 is fixed to the distal end of the tube 108B.

Figure 3A:
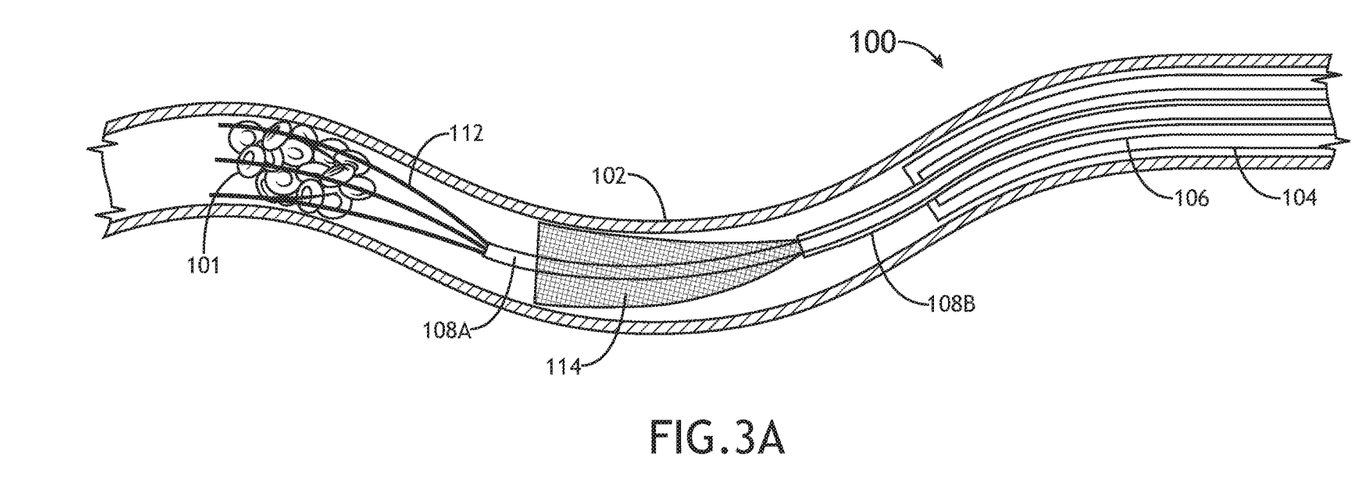
FIG. 3A illustrates a cross-sectional side view of the obstruction removal system, wherein an expandable member of the obstruction removal device is fixed to the distal end of a tube, and a removal tool of the obstruction removal device is fixed to a distal end of a guide wire that is disposed within the tube, in accordance with one or more embodiments of the present disclosure.

As shown in FIG. 3A, the guide wire 108A may be configured to be at least partially extended from a distal end of the tube 108B. In such embodiments, the guide wire 108A may be configured to extend the removal tool 112 away from the expandable member 114 (by extending the guide wire 108A further into the vasculature 102 and/or pulling the tube 108B back). This may allow the removal tool 112 to at least partially separate the obstruction 101 from the inner surface of the vasculature 102 without interference from the expandable member 114.

Figure 3B:
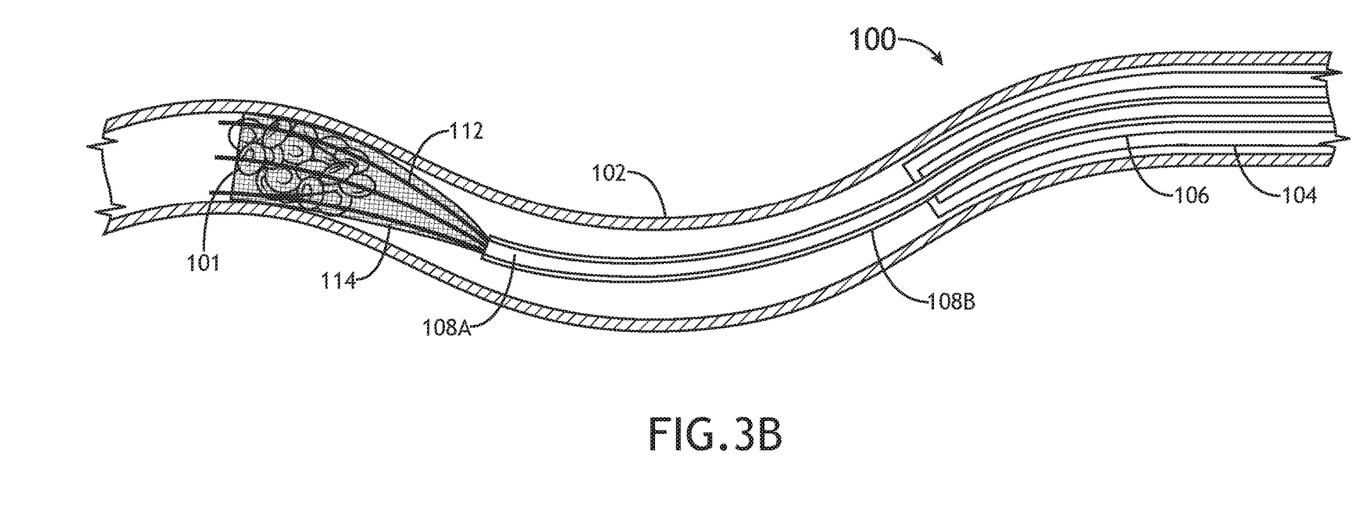
FIG. 3B illustrates a cross-sectional side view of the obstruction removal device of FIG. 3A, where the expandable member is slid over at least a portion of the removal tool by pushing the tube along the guide wire and/or pulling the guide wire into the tube, in accordance with one or more embodiments of the present disclosure.
Figure 3C:
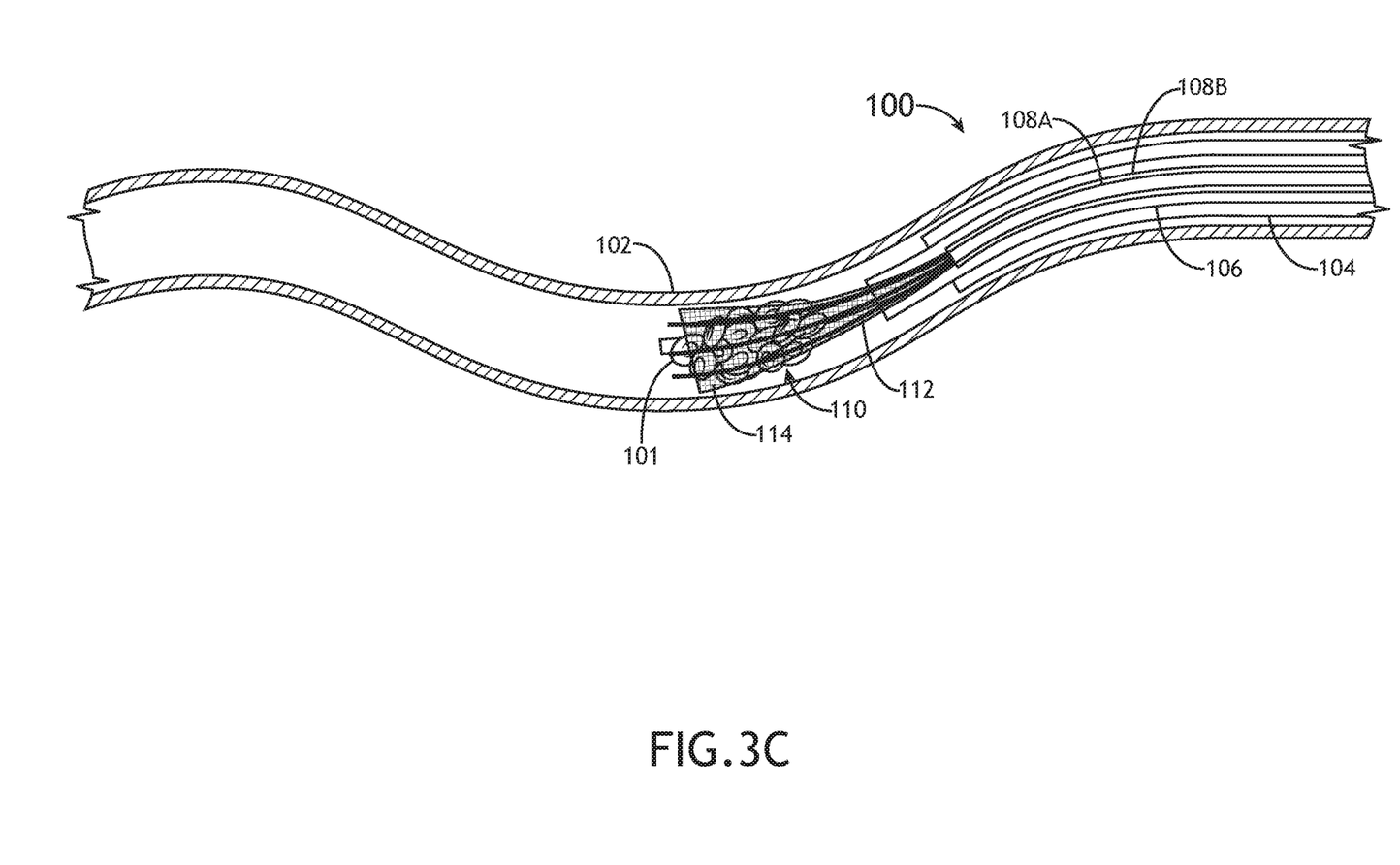
FIG. 3C illustrates a cross-sectional side view of the obstruction removal device of FIG. 3A and the intermediate catheter of the obstruction removal system being pulled back through the guide catheter to remove the obstruction from the vasculature, in accordance with one or more embodiments of the present disclosure.

Referring now to FIG. 3B, the guide wire 108A may be further configured to retract the removal tool 112 toward the expandable member 114 (by pulling the guide wire 108A back into the tube 108B and/or pushing the tube 108B along the guide wire 108A) so that the expandable member 114 at least partially surrounds the removal tool 112 and/or obstruction 101 after the removal tool 112 at least partially separates the obstruction 101 from the inner surface of the vasculature 102. Then, as shown in FIG. 3C, the intermediate catheter 106 may be pushed forward and/or the delivery tool 108 (i.e., guide wire 108A and tube 108B) may be pulled back relative to the intermediate catheter 106 to at least partially re-sheathe the obstruction removal device 110 so that the expandable member 114 compresses the removal tool 112, thereby causing the removal tool 112 to grasp the obstruction 101. The intermediate catheter 106 with the delivery tool 108, the obstruction removal device 110 (including removal tool 112 and expandable member 114), and the obstruction 101 are then pulled back through the guide catheter 104 to remove the obstruction 101 from the vasculature 102. Alternatively, the delivery tool 108 with the obstruction removal device 110 and the obstruction 101 may be pulled directly through the guide catheter 104 (without use of an intermediate catheter 106).

Referring generally to embodiments of the obstruction removal system 100 disclosed herein, the expandable member 114 may be configured to transition between a first configuration and a second configuration, or between a contracted state and an expanded state, in any number of ways, including, but not limited to, unsheathing (e.g., withdrawal of the intermediate catheter 106 or extension through the guide catheter 104), disengagement of locking members (e.g., wires, hooks, etc.) attached to the expandable member 114, use of shape memory alloys (e.g., Nitinol), or the like. It is envisioned that when the expandable member is in an expanded state, the expandable member may take up a substantial portion of the cross-section of the vasculature 102.

In embodiments, the expandable member 114, removal tool 112, and the obstruction 101 are withdrawn into the guide catheter 104 and removed from the vasculature 102. In some embodiments, the expandable member 114, removal tool 112, and the obstruction 101 may be further withdrawn into the intermediate catheter 106. The expandable member 114 may surround at least a portion of the obstruction 101 to prevent dislodging and may also assist in compressing the obstruction 101 into the guide catheter 104 and/or the intermediate catheter 106 (e.g., by tension, cinching, crimping, etc.).

Surrounding at least a portion of the removal tool 112 and/or obstruction 101 with the expandable member 114 may serve several functions including, but not limited to, reducing a likelihood that the removal tool 112 snags (e.g. on an inner surface/vessel wall of the vasculature 102 or an opening of the guide catheter 104), reducing a profile of the obstruction 101 for removal through the guide catheter 104 and/or intermediate catheter 106, and/or securing the obstruction 101 to prevent dislodgement from the removal tool 112.

In embodiments, the expandable member 114 may comprise a wire mesh. Such a wire mesh may include wires made of a flexible material (e.g. nitinol, cobalt chromium, polymer mesh (e.g., PET or nylon), or the like), where the wires (e.g. 16 to 288 or more wires), have a certain diameter (e.g. from 0.0007 inches to 0.0050 inches), and have certain material properties (e.g. strength, coefficient of friction with blood, resistance to plastic deformation, etc.) suitable for engaging the obstruction 101 and/or removal tool 112. The wire mesh can be can be single ply or multiple plies. Furthermore, the wire mesh may include various sets of wires (e.g. support wires with larger diameters, wires to engage a vessel wall, wires to engage a portion of the obstruction or obstruction removal device, radiopaque or radiodense wires, etc.).

The peeler wires 116 that help to separate the obstruction 101 from the inner surface of the vasculature 102 may comprise metal wires (e.g., elastic or super-elastic Nitinol wire ranging in diameter from 0.001 inches to 0.010 inches, or more, in diameter). In embodiments, the peeler wires 116 and/or hook wires 118 may be made from round Nitinol wire, flat ribbon Nitinol wire, and/or cut from a Nitinol tube. In some embodiments, the peeler wires 116 are made of round wire segments to provide a smooth and atraumatic surface that does not damage the inner surface (vessel wall) of the vasculature 102.

The removal tool 112 may include any number of peeler wires 116 and hook wires. In some embodiments, the removal tool 112 includes three to nine, or more, peeler wires 116. Each peeler wire 116 may have at least one hook wire 118 extending or jutting out from the peeler wire 116. Alternatively, only a subset of the peeler wires 116 may have hook wires 118 extending or jutting out for the purpose of securing the obstruction 101 after the obstruction 101 is removed from the inner surface of the vasculature 102.

In some embodiments, the leading edge of the expandable member 114 may include the peeler wires 116 of the removal tool 112 that may extend distal to the leading edge, may be flush with the leading edge, or may be recessed. Alternatively, as shown in FIGS. 3A through 3C, the expandable member 114 and the removal tool 112 may be separable.

Any number of the presently disclosed elements may be suitable for imaging by a non-invasive imaging technology (e.g. X-ray, CT scans, etc.). For instance, the guide catheter 104, intermediate catheter 106, delivery tool 108, removal tool 112, expandable member 114, and/or any additional components may comprise radiodense or radiopaque material (e.g. titanium, tungsten, barium sulfate, or zirconium oxide) suitable for insertion in a human body.

It is to be understood that any number of components of the obstruction removal system 100 may be attached by any suitable means including, but not limited to, welding, adhesive, mechanical fastening, interference fittings, etc. For example, the deliver tool 108 may be attached to the removal tool 112 and/or expandable member 114 by such means. Alternatively, or additionally, two or more of the components may be portions of a common structure (e.g., a common mold or print).

It is envisioned that there may be multiple orders in which one or more devices of the obstruction removal system 100 are deployed. Factors for determining an order may include, but are not limited to, vasculature properties (e.g. vasculature size, vasculature geometries, branches of the vasculature, vasculature wall strength, etc.), blood pressure, blood flow direction, duration of operation (i.e. does patient require a reduced operating time for safety concerns), size of obstruction, or the configuration of the obstruction removal device.

Referring generally to FIGS. 1A through 3C, a method of removing an obstruction from a vasculature 102 may include, but is not limited to, the steps of: deploying the guide catheter 104 through the patient's vasculature 102 to a position near the obstruction 101; extending the delivery tool 108 with the end-mounted obstruction removal device 110 through the guide catheter 104 so that the distal end of the delivery tool 108 is disposed proximate to the obstruction 101 in the vasculature 102 (with/without the use of the intermediate catheter 106); engaging at least one portion of the obstruction 101 in the vasculature 102 with the removal tool 112 of the obstruction removal device 110; and grasping at least one portion of the removal tool 112 and the obstruction 101 with the expandable member 114 of the obstruction removal device 110, where the expandable member 114 transitions from an expanded state to a contracted state when the delivery tool 108 is at least partially withdrawn into the guide catheter 104 and/or intermediate catheter 106 to remove the removal tool 112 and the obstruction 101 from the vasculature 102.

It is to be understood that implementations of the methods disclosed herein may include one or more of the steps described herein. Further, such steps may be carried out in any desired order and, in some implementations, two or more of the steps may be carried out simultaneously with one another. Two or more of the steps disclosed herein may be combined in a single step, and in some implementations, one or more of the steps may be carried out as two or more sub-steps. Further, other steps or sub-steps may be carried in addition to, or as substitutes to one or more of the steps disclosed herein.

It is also to be understood that usage of terminology in the present disclosure is not intended to be limiting. For example, as used herein, an "obstruction" may refer to any vascular obstruction, including but not limited to, a blood clot, plaque (e.g. fat, cholesterol, etc.), internal structure/growth, foreign object, or the like.

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:
1. An obstruction removal system, comprising:
  a guide catheter configured to be inserted within a vasculature;
  a delivery tool having a distal end configured to be inserted within the guide catheter and disposed proximate to an obstruction in the vasculature;
  a removal tool disposed at the distal end of the delivery tool, with a proximal end of the removal tool being coupled to the distal end of the delivery tool so that the removal tool extends distally into the vasculature from the distal end of the delivery tool, the removal tool comprising peeler wires and hook wires that are configured to at least partially separate the obstruction from an inner surface of the vasculature, wherein the peeler wires comprise non-braided wire segments that extend from the distal end of the delivery tool toward the inner surface of the vasculature when the removal tool is deployed within the vasculature, and the hook wires comprise curved wire segments that extend from respective wire segments of the peeler wires toward a central axis of the removal tool; and an expandable member comprising wire mesh coupled to the delivery tool and configured to surround most of the removal tool from the proximal end of the removal tool toward a distal end of the removal tool, wherein the expandable member is configured to grasp at least one portion of the removal tool and the obstruction as the expandable member transitions from an expanded state to a contracted state when the delivery tool is removed from the vasculature to remove the removal tool and the obstruction from the vasculature, and wherein, in the contracted state, the expandable member compresses the peeler wires of the removal tool toward one another so that the removal tool clenches the obstruction in between the peeler wires.

2. The obstruction removal system of claim 1, further comprising:
an intermediate catheter configured to sheathe the removal tool and the expandable member while the delivery tool is inserted within the guide catheter and guided into the vasculature.

3. The obstruction removal system of claim 2, wherein the intermediate catheter is further configured to unsheathe the removal tool and the expandable member to allow the removal tool to at least partially separate the obstruction from the inner surface of the vasculature.

4. The obstruction removal system of claim 3, wherein the intermediate catheter is further configured to at least partially re-sheathe the removal tool and the expandable member to cause the expandable member to transition from the expanded state to the contracted state so that the expandable member grasps the at least one portion of the removal tool and the obstruction when the delivery tool is removed from the vasculature to remove the removal tool and the obstruction from the vasculature.

5. The obstruction removal system of claim 1, wherein the delivery tool comprises a guide wire or a tube, wherein the expandable member and the removal tool are both fixed to the distal end of the guide wire or the tube.

6. The obstruction removal system of claim 1, wherein the delivery tool comprises a guide wire disposed within a tube and configured to be at least partially extended from a distal end of the tube, wherein the expandable member is fixed to the distal end of the tube, and wherein the removal tool is fixed to a distal end of the guide wire.

7. The obstruction removal system of claim 6, wherein the guide wire is configured to extend the removal tool away from the expandable member to allow the removal tool to at least partially separate the obstruction from the inner surface of the vasculature, and wherein the guide wire is further configured to retract the removal tool toward the expandable member so that the expandable member at least partially surrounds the removal tool and the obstruction after the removal tool at least partially separates the obstruction from the inner surface of the vasculature.

8. An obstruction removal device, comprising:
a removal tool configured to be disposed at a distal end of a delivery tool, with a proximal end of the removal tool being coupled to the distal end of the delivery tool so that the removal tool extends distally into a vasculature from the distal end of the delivery tool, the removal tool comprising peeler wires and hook wires that are configured to at least partially separate an obstruction from an inner surface of the vasculature, wherein the peeler wires comprise non-braided wire segments that extend from the distal end of the delivery tool toward the inner surface of the vasculature when the removal tool is deployed within the vasculature, and the hook wires comprise curved wire segments that extend from respective wire segments of the peeler wires toward a central axis of the removal tool; and an expandable member comprising wire mesh coupled to the delivery tool and configured to surround most of the removal tool from the proximal end of the removal tool toward a distal end of the removal tool, wherein the expandable member is further configured to grasp at least one portion of the removal tool and the obstruction as the expandable member transitions from an expanded state to a contracted state when the delivery tool is removed from the vasculature to remove the removal tool and the obstruction from the vasculature, and wherein, in the contracted state, the expandable member compresses the peeler wires of the removal tool toward one another so that the removal tool clenches the obstruction in between the peeler wires.

9. The obstruction removal device of claim 8, wherein the expandable member is fixedly coupled to the removal tool.

10. The obstruction removal device of claim 8, wherein the expandable member and the removal tool are moveable independent of one another.

* * * * *